Sept. 4, 1956 J. D. BROWNELL Plant Pat. 1,510
ROSE PLANT
Filed June 7, 1955
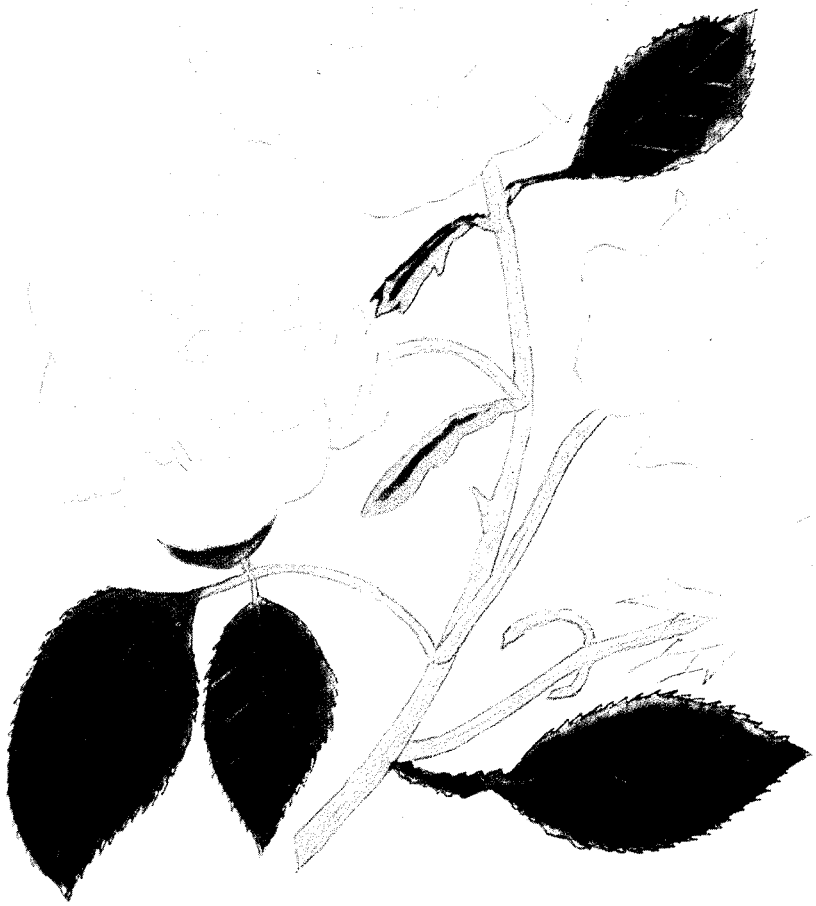
INVENTOR.
Josephine D. Brownell United States Patent Office Plant Pat. 1,510
Patented Sept. 4, 1956

1,510

ROSE PLANT

Josephine D. Brownell, Little Compton, R. I.

Application June 7, 1955, Serial No. 513,922

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by selection of variety variations and by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States;

The pink, orange and yellow colors (ordinarily dictionary definition) of its petals, in combination with the unique brilliance thereof and their tendency to hold this color under exposure;

The novelty and variation within certain definite limits of the form of the bloom, its character of holding that form for a long time and the petallage of the flowers;

Its character of fragrance;

Its unusual abundance of flowers, notable after early bloom time and until frost;

The intensity of its remontant and everblooming or reblooming character and the large size of its bloom;

Its character of ascending in height by recurrent branching and progressively longer stems from the base.

The character of producing some seven leafleted leaves; which character seldom has obtained on hybrid teas not having *Rosa wichuraiana* ancestry, but frequently obtains on flower stems of descendants of *Rosa wichuraiana* of the dwarf reblooming type.

In the accompanying drawing forming a part of this specification I have shown my new rose in its natural colors, that is, as near as is possible to do so artificially.

My new rose is otherwise described as follows:

ESSENTIAL INFORMATION

*Type*

Hybrid tea, *Rosa wichuraiana* hybrid, dwarf ascending under normal conditions to about four feet tall, for garden display, cut flower and forcing or growing under glass.

*Class*

Hybrid tea crossed with *Rosa wichuraiana* hybrid, further restricted by originator to include only those varieties that can survive moderately low sub-zero temperatures.

*Breeding*

This variety was produced and bred by me and under my direction by propagation, selection and cross pollenation.

It came into being as a seedling, the pollen parent of which was Sutter's Gold, Plant Patent No. 885, and the seed parent was an unnamed seedling descendant from *Rosa wichuraiana.*

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 7, 1950.[1] The seed was planted for me and under my direction on December 23, 1950, and the date of the first flower was July 1, 1951.

The plant and flower seemed to me to be of unusual merit and I have since made and directed extensive propogations and tests thereof.

Plants of this variety budded from this seedling on to *Rosa multiflora* root stocks, have after being exposed to moderate subzero temperatures, survived and bloomed normally the following season in the hybrid tea manner. The variety has been propagated by budding at Little Compton, Rhode Island, on August 21, 1951, and September 3, 1952, and thereafter and characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three and occasionally more on each stem, in the usual hybrid tea type of cluster; of a more free flowering type than many commercial varieties of hybrid teas.

The pedicels and peduncles are medium in diameter and medium in length, erect, stiff, almost smooth, free from large prickles and bristles. Stems are long, diameter medium and moderately stiff and rigid.

*Quantity of bloom*

Free, being cumulative in quantity from year to year as the plant increases in size, flowering through the summer and fall.

*Fragrance*

Distinctive, pleasing china tea in combination with that of *Rosa wichuraiana,* under favorable environment.

*Bud*

Neck normal as described, opens well, being a little to not at all affected at high temperatures; the color is less intense and the form of the petals is less recurled.

Before the calyx separates the size is medium, form moderately high pointed, the sepals are normal except with occasional spurs often on two sides opposite to each other; or irregularly spaced and distributed; otherwise tapering to lanceolate at their apex, turning back nearly perpendicular to the pedicel as the bud opens, later turning more downward.

Color of the bud as calyx opens, outside Indian Yellow at 6/2; overlaid at tip and somewhat toward base with Saturn Red at 13/3 extending with less intensity toward the base; color reference to English Horticultural Color Chart.[2]

*Bloom*

As petals open outside color of petals as above gradually softening in intensity as flower opens. Inner side of petals Buttercup Yellow at 5/2 at base, shading upward

[1] This and other dates herein are approximate.
[2] Color reference to same unless otherwise indicated.

toward tip to Saturn Red at 13/2, occasionally deeper to 13/1. These colors on the inside soften slowly as the flower ages, often ending at tip nearly Mandarin Red 17/2, later softening to 17/3.

Color slightly variable dependent upon quality of sun or other light.

The flower usually varies in size averaging around five inches in diameter when fully open, number of petals varying around forty, frequently some smaller petals and petaloids in the center, variable in form and number. Upper edges of most petals irregular, waved, a few with pointed apex.

The flower opens moderately ovate and medium high centered, quite formal, with late display of stamens and pistils. The petals are nearly formal as to arrangement. Texture is medium to thick; both sides brilliant. The time of opening in favorable conditions is about five days.

The petals are substantial and after about six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Productive organs*

Stamens, quantity variable to scarce, medium long of slightly uneven length.

Anthers, nearly Orpiment Orange at 10/1. Filaments, nearly Amber Yellow, at 305/3.

Pistils are several of nearly even length, averaging about one-half inch long.

PLANT

*Foliage*

Is abundant, of compound leaves of three to five leaflets near the flower, five leaflets lower down the stem and occasionally seven leaflets in the middle of the stems and nearer the base. Often with short narrow leafy formations variously positioned near the flower as shown. Size of leaflets medium to large. Form of leaflets usually nearly ovate with apex moderately acute, base rounded to slightly pointed in some instances; margins with slightly irregular medium pointed serrations, petiolules medium short, and with slightly wider space than usual between leaflets.

The leaflets average in width about one-half of their length.

Color of leaflets on the upper surface is slightly variable from Spinach Green at o960, irregularly shaded with Parsley Green at oo962, with reverse side nearly Asphodel Green, the last color reference is to Robert Ridgway Color Standards.

The rachises are moderately narrow to slender, upper side, overlaid with Crimson 22/3, smooth except some very short hairs almost microscopic on edges. Under side moderately smooth, usually three to five short prickles.

Stipules are variable from normal medium short.

Plant habit, dwarf, becoming bushy to tall for a hybrid tea; from two and one-half to three and one-half feet in height, by stems from the base and by rebranching and growth and enlargement and extension of the stems. The growth is moderately free at first, developing more rapidly after one or two years under favorable vegetative opportunity.

Color of mature stems is Scheeles Green at 860/3, with a slight overlay of Crimson at 22/3.

Prickles, several, frequently two to three between leaves, averaging in length about one-quarter to one-third inch, shading from Carmine at 21/2 to lighter at the base, turning lighter throughout and later to nearly colorless.

COMPARISONS

This rose variety is one of a new race or type of rose, not found in nature, being a *Rosa wichuraiana* hybrid tea hybrid.

The variety most nearly resembling my new rose known to your applicant is Shades of Autumn, Plant Patent No. 542; in that my new rose is of a different color, inside of petals being less pink and more yellow and outside of petals being more pink of a more brilliant shade of yellow. The leaflets of my new rose average much larger than those of Shades of Autumn and the serrations thereof are more pronounced and the upper edges of the petals are more irregular.

My new rose has a different fragrance.

I claim:

A new and distinct variety of rose plant, substantially as shown and described characterized by its color pattern, fragrance, form and color and its Wichuraiana traits.

No references cited.